United States Patent [19]

Noguchi

[11] Patent Number: 5,812,223
[45] Date of Patent: Sep. 22, 1998

[54] COLOR LCD PROJECTOR WITH THREE COLOR SEPARATING POLARIZING BEAM SPLITTERS

[75] Inventor: Masato Noguchi, Tokyo, Japan

[73] Assignee: Asahi Kogaku Kogyo Kabushiki Kaisha, Tokyo, Japan

[21] Appl. No.: 800,151

[22] Filed: Feb. 13, 1997

Related U.S. Application Data

[63] Continuation of Ser. No. 607,569, Feb. 27, 1996, abandoned, which is a continuation of Ser. No. 819,757, Jan. 13, 1992, abandoned.

[30] Foreign Application Priority Data

Feb. 28, 1995 [JP] Japan .................................... 7-064866

[51] Int. Cl.[6] .......................... G02F 1/1335; G03B 21/00
[52] U.S. Cl. ...................................... 349/9; 349/8; 353/31
[58] Field of Search ......................... 359/40, 41; 353/31, 353/30; 349/5, 8, 9

[56] References Cited

U.S. PATENT DOCUMENTS

| | | | |
|---|---|---|---|
| 4,461,542 | 7/1984 | Gagnon | 359/41 |
| 4,826,311 | 5/1989 | Ledebuhr | 359/40 |
| 4,904,061 | 2/1990 | Aruga | 359/40 |
| 5,022,750 | 6/1991 | Flasck | 359/41 |
| 5,098,183 | 3/1992 | Sonehara | 353/31 |
| 5,179,398 | 1/1993 | Iizuka | 353/30 |
| 5,231,433 | 7/1993 | Yoshida et al. | 353/63 |
| 5,267,029 | 11/1993 | Kurematsu et al. | 359/41 |
| 5,283,599 | 2/1994 | Tejima et al. | 353/30 |
| 5,305,029 | 4/1994 | Yoshida et al. | 353/31 |
| 5,381,197 | 1/1995 | Yoshida et al. | 353/98 |
| 5,446,510 | 8/1995 | Mitsutake et al. | 359/40 |
| 5,530,489 | 6/1996 | Henderson et al. | 359/40 |

FOREIGN PATENT DOCUMENTS

4-113309  4/1992  Japan .

*Primary Examiner*—William L. Sikes
*Assistant Examiner*—Toan Ton
*Attorney, Agent, or Firm*—Greenblum & Bernstein, P.L.C.

[57] ABSTRACT

An LCD projector which has a white light source for emitting a randomly polarized luminous flux, and a plurality of LCD panels for modulating luminous fluxes that are transmitted through the LCD panels. The LCD projector also includes four reflecting devices. The first reflecting device reflects a first portion of the luminous flux having a first polarization characteristic and a wavelength which is within a first predetermined range of wavelengths, to the first LCD panel. The second reflecting device reflects a second portion of the luminous flux that is not reflected to the first LCD panel, to the second LCD panel. The second portion of the luminous flux has the first polarization characteristic and a wavelength which is within a second predetermined range of wavelengths. The third reflecting device reflects a third portion of the luminous flux that is not reflected to the second LCD panel, to the third LCD panel. The third portion of the luminous flux has the first polarization characteristic and a wavelength which is within a third predetermined range of wavelengths. The fourth reflecting device reflects a fourth portion of the luminous flux that is not reflected to the third LCD panel, to the fourth LCD panel. The fourth portion of the luminous flux has a second polarization characteristic.

20 Claims, 4 Drawing Sheets

COLOR LCD PROJECTOR WITH THREE COLOR SEPARATING POLARIZING BEAM SPLITTERS

This application is a continuation of application Ser. No. 08/607,569, filed Feb. 27, 1996, now abandoned, which is a con. of Ser. No. 08/819,757, filed Jan. 13, 1992, now abn.

BACKGROUND OF THE INVENTION

The present invention relates to an LCD (liquid crystal display) projector for projecting a color image onto a screens and a method by which the luminous flux is projected onto the screen.

Conventionally, a color LCD projector has a light source which emits randomly polarized white light. The randomly polarized luminous flux emitted by the white light source is separated into three luminous flux components (i.e. blue light, green light, and red light) using a plurality of dichroic mirrors. Each of the luminous flux components is transmitted through an LCD panel, which modulates the luminous flux in accordance with image data provided by a video signal. The luminous flux components are then recombined and projected onto a screen. A polarizing plate is arranged between the light source and the LCD panel for making the polarizing direction of the luminous flux that is incident on each of the LCD panels uniform. Due to light loss caused by the polarizing plate, the amount of light projected onto the screen is equivalent to half of the light generated by the light source. Therefore, the screen is dark in comparison to the amount of light emitted by the light source.

Figure 1:
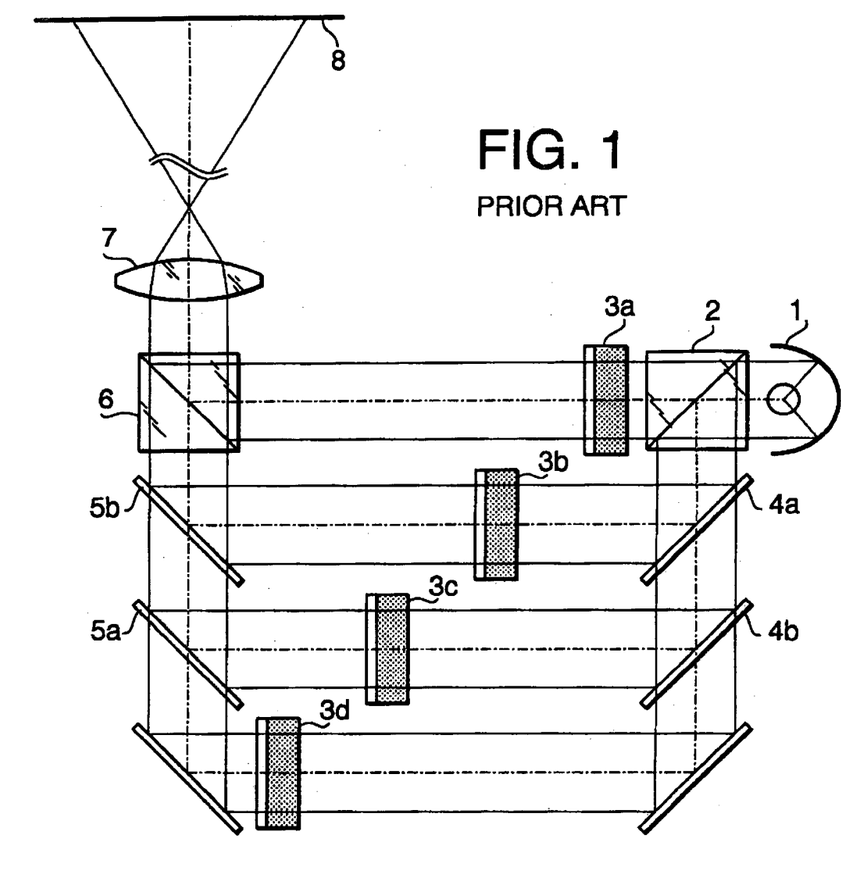
FIG. 1 shows a schematic diagram of a conventional LCD projector.

In order to solve this problem, an LCD projector has been proposed where substantially all of the light from the light source is projected onto the screen. As shown in FIG. 1, in this type of projector, the luminous flux generated by a light source 1 is incident onto a polarizing beam splitter 2. A P-polarized light component passes through the polarization beam splitter 2 and is incident onto an LCD panel 3a. Further, an S-polarized light component that is reflected by the polarization beam splitter 2 is color separated by dichroic mirrors 4a and 4b and is incident on red, green and blue LCD panels 3b, 3C, and 3d, respectively. The luminous fluxes which pass through each of the LCD panels 3a, 3b, 3C, and 3d are modulated with the image data provided by the video signal, and then are combined into a single luminous flux by dichroic mirrors 5a, 5b and polarization beam splitter 6. Then, the combined luminous flux is projected onto a screen 8 by a projecting lens 7.

Figure 2:
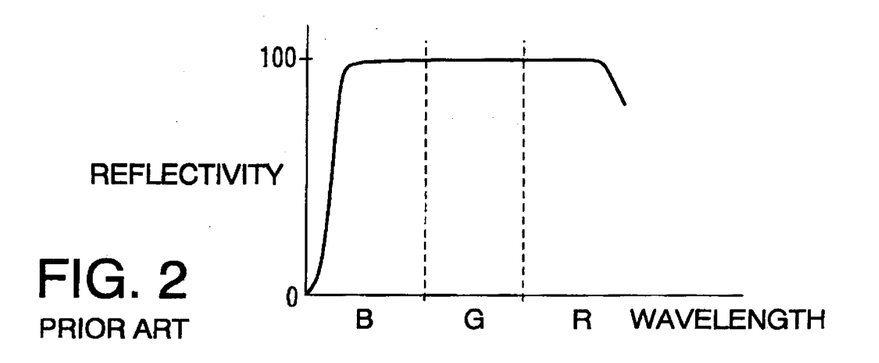
FIG. 2 shows a graph of a reflection characteristic of a polarization beam splitter of the conventional LCD projector shown in FIG. 1.

The polarization beam splitter 2 is required to have a reflection characteristic of the S-polarized light, as shown in FIG. 2, in which all the visible light is completely reflected. This is necessary if the transmitted light and the reflected light are to both be white light.

However, when the design of the coating used in the polarization beam splitter 2 is taken into consideration, it is difficult for the polarization beam splitter 2 to have the ideal spectral reflection characteristics as shown in FIG. 2. Thus, it is possible that the polarization beam splitter 2 will not be able to completely reflect all of the light over the entire visible range. If the S-polarized light component in the visible range passes through the polarization beam splitter 2 and is incident on the brightness LCD panel 3a, then the P-polarized light is projected as luminous flux having brightness and darkness characteristics which are reversed. As a result, the brightness distribution for the projected image may be disturbed.

Further, it may be possible for the polarization beam splitter 2 to have the ideal spectral reflection characteristics, but this will require expensive and precise design and manufacturing technology, which will increase the cost of manufacturing the polarization beam splitter. Therefore, the manufacturing cost of the entire LCD projector will be substantially increased.

SUMMARY OF THE INVENTION

It is therefore an object of the invention to provide an LCD projector capable of obtaining a stable image with a relatively inexpensive polarization beam splitter while employing a method for projecting a luminous flux onto a screen where substantially all of the light generated by the light source is utilized.

According to a first aspect of the present invention, an LCD projector is provided which includes a white light source for emitting a randomly polarized luminous flux, and a plurality of LCD panels for modulating luminous fluxes that are transmitted through the LCD panels. The LCD projector also includes four reflecting devices. The first reflecting device reflects a first portion of the luminous flux having a first polarization characteristic and a wavelength which is within a first predetermined range of wavelengths, to the first LCD panel. The second reflecting device reflects a second portion of the luminous flux that is not reflected to the first LCD panel, to the second LCD panel. The second portion of the luminous flux has the first polarization characteristic and a wavelength which is within a second predetermined range of wavelengths. The third reflecting device reflects a third portion of the luminous flux that is not reflected to the second LCD panel, to the third LCD panel. The third portion of the luminous flux has the first polarization characteristic and a wavelength which is within a third predetermined range of wavelengths. The fourth reflecting device reflects a fourth portion of the luminous flux that is not reflected to the third LCD panel, to the fourth LCD panel. The fourth portion of the luminous flux has a second polarization characteristic.

Thus, in the preferred embodiment of the present invention, the luminous flux is separated into three luminous fluxes having different wavelength ranges. Further, each of the three luminous fluxes have the same polarization characteristic. Therefore, by utilizing the four reflecting devices having the above spectrum reflection characteristics, the cost of manufacturing each of the reflecting devices can be reduced, and therefore the cost of manufacturing the LCD projector can also be reduced.

Optionally, the LCD projector further includes three combining devices for combining the separated luminous fluxes. The first combining device combines the modulated third portion of the luminous flux transmitted through the third LCD panel with the modulated fourth portion of the luminous flux transmitted through the fourth LCD panel, into a first combined luminous flux. The second combining device combines the modulated second portion of the luminous flux transmitted through the second LCD panel with the first combined luminous flux, into a second combined luminous flux. The third combining device combines the modulated first portion of the luminous flux transmitted through the first LCD panel with the second combined luminous flux, into a third combined luminous flux. The LCD projector also includes a device for projecting the third combined luminous flux onto a screen.

Thus, after the LCD panels have modulated the respective luminous fluxes in accordance with image data supplied from a video signal, the modulated luminous fluxes are recombined into a single luminous flux, and projected onto a screen.

In a preferred embodiment, the fourth reflecting device includes a mirror for reflecting the fourth luminous flux to the fourth LCD panel.

Alternately, the LCD projector further includes another mirror for reflecting the modulated fourth portion of the luminous flux transmitted through the fourth LCD panel to the first combining device.

In the LCD projector according to the present invention, the first portion of the luminous flux reflected by the first reflecting device has a wavelength which is shorter than a first predetermined wavelength. Similarly, the second portion of the luminous flux reflected by the second reflecting device has a wavelength which is shorter than a second predetermined wavelength, where the second predetermined wavelength is longer than the first predetermined wavelength. Further, the third portion of the luminous flux reflected by the third reflecting device has a wavelength which is longer than the second predetermined wavelength.

In this case, the first predetermined wavelength is a blue-green border wavelength, and the second predetermined wavelength is a green-red border wavelength.

In the preferred embodiment, the first reflecting device, the second reflecting device and the third reflecting device each include a polarization beam splitter. Each polarization beam splitter reflects S-polarized luminous flux in which the electric vector is polarized perpendicular to the incident plane of the first polarization beam splitter, and transmits P-polarized luminous flux in which the electric vector is polarized parallel to the incident plane of the first polarization beam splitter.

Further, each of the combining devices also includes a polarization beam splitter which has a similar spectrum reflection characteristic to a polarization beam splitter of a corresponding reflecting device. Therefore, the number of different polarization beam splitters that are required to manufacture the LCD projector is reduced.

In the preferred embodiment, the first reflecting device is arranged such that an angle of incidence of the luminous flux on the first reflecting device is equivalent to the Brewster Angle. Further, the second reflecting device, the third reflecting device and the fourth reflecting device are arranged to be parallel to the first reflecting device.

According to another aspect of the present invention, there is provided an LCD projector which includes a light source for emitting a luminous flux having randomly polarized white light, and three polarization beam splitters. The first polarization beam splitter has a spectrum reflection characteristic for reflecting one of red light and blue light of the luminous flux having a first polarization characteristic. A remaining portion of the luminous flux is transmitted through the first polarization beam splitter. The second polarization beam splitter has a spectrum reflection characteristic for reflecting a portion of the luminous flux transmitted by the first polarization beam splitter having green light having said first polarization characteristic. Another remaining portion of the luminous flux is transmitted through the second polarization beam splitter. The third polarization beam splitter has the spectrum reflection characteristic for reflecting a portion of the luminous flux transmitted by the second polarization beam splitter having the other of the red light and the blue light having said first polarization characteristic, and which is not reflected by the first polarization beam splitter. A third remaining portion of the luminous flux is transmitted through the third polarization beam splitter. The LCD projector also includes three LCD panels, each of the LCD panels modulating one of the reflected light components, and a fourth LCD panel for modulating a light component having a second polarization characteristic which is transmitted through the third polarization beam splitter.

According to a further aspect of the present invention, there is provided a method for separating a randomly polarized luminous flux generated by a white light source in an LCD projector into various light components having different wavelength ranges and polarization states. The method includes the steps of:

reflecting a first portion of the luminous flux having a first polarization characteristic and a wavelength which is within a first predetermined range of wavelengths, to a first LCD panel;

reflecting a second portion of the luminous flux that is not reflected to the first LCD panel, to a second LCD panel, the second portion of the luminous flux having the first polarization characteristic and a wavelength which is within a second predetermined range of wavelengths;

reflecting a third portion of the luminous flux that is not reflected to the second LCD panel, to a third LCD panel, the third portion of the luminous flux having the first polarization characteristic and a wavelength which is within a third predetermined range of wavelengths; and reflecting a fourth portion of the luminous flux that is not reflected to the third LCD panel, to a fourth LCD panel, the fourth portion of the luminous flux having a second polarization characteristic.

DESCRIPTION OF THE PREFERRED EMBODIMENTS

Figure 3:
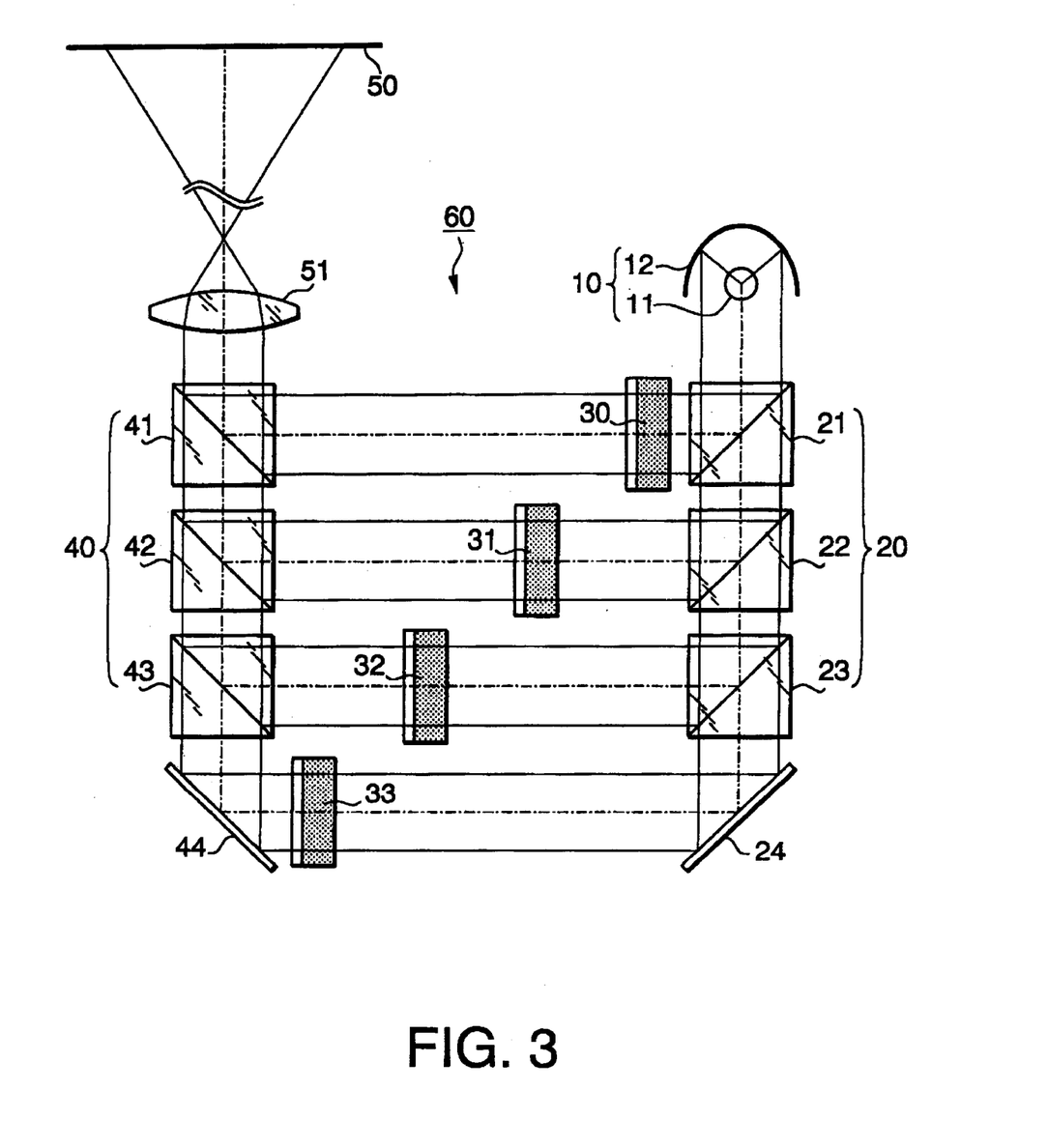
FIG. 3 shows a schematic diagram of a first embodiment of an LCD projector according to the present invention.

FIG. 3 shows an optical system of a first embodiment of an LCD projector 60 which embodies the present invention. The LCD projector 60 includes a light source unit 10, a polarization beam splitter group 20, four LCD panels 30, 31, 32, and 33, polarization beam splitter group 40, and a projecting lens 51.

The light source unit 10 has a light source 11, such as a Xenon lamp which generates randomly polarized white light, and a concave mirror 12 for reflecting the luminous flux generated by the light source 11, in one direction.

The polarization beam splitter group 20 separates the luminous flux generated by the light source unit 10 into separate color luminous fluxes. The polarization beam splitter group 20 includes three polarization beam splitters 21, 22, and 23. Each of the polarization beam splitters 21, 22, and 23 is of a cube prism type.

Three separate S-polarized luminous fluxes are transmitted through the three LCD panels 30, 31, and 32, respectively. In this specification, S-polarized luminous fluxes are polarized such that the electric vector is perpendicular to an incident plane.

Each LCD panel modulates the respective luminous flux in order that the desired image from a video source may be projected. A P-polarized luminous flux, which is transmitted through the polarization beam splitter 21 is transmitted to a brightness LCD panel 33. In this specification, the P-polarized luminous flux is polarized such that the electric vector is parallel to the incident plane.

After the three S-polarized luminous fluxes and the P-polarized luminous flux have been modulated by the LCD panels 30, 31, 32 and 33, respectively, the luminous fluxes are recombined into a single luminous flux by the polarization beam splitter group 40. The single luminous flux is then incident on a projection lens 51, which projects the color image onto a screen 50.

The polarization beam splitter group 20, the LCD panels 30 through 34 and the polarization beam splitter group 40 will be described in more detail below.

As mentioned above, the polarization beam splitter group 20 includes the polarization beam splitters 21 through 23. The polarization beam splitter 21 reflects the S-polarized light components that have a shorter wavelength than a blue-green wavelength $\lambda 1$. The blue-green wavelength $\lambda 1$ borders the blue light component and the green light component. In the preferred embodiment $\lambda 1$ is approximately 500 nm.

The polarization beam splitter 22 reflects the S-polarized light components that have a shorter wavelength than a green-red wavelength $\lambda 2$. The green-red wavelength $\lambda 2$ borders the green light component and the red light component. In the preferred embodiment $\lambda 2$ is approximately 600 nm.

The polarization beam splitter 23 reflects the S-polarized light which has passed through the polarization beam splitters 21, 22, in order as viewed from the light source side.

Figure 4A:
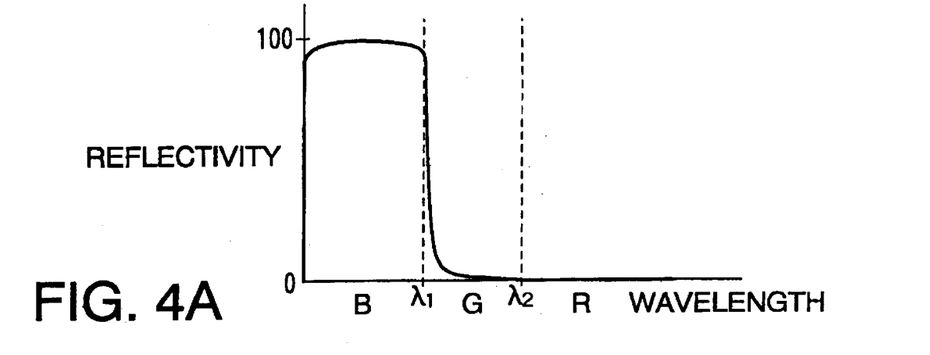
FIGS. 4A, 4B and 4C show graphs of reflection characteristics of polarization beam splitters of the LCD projector shown in FIG. 3.
Figure 4B:
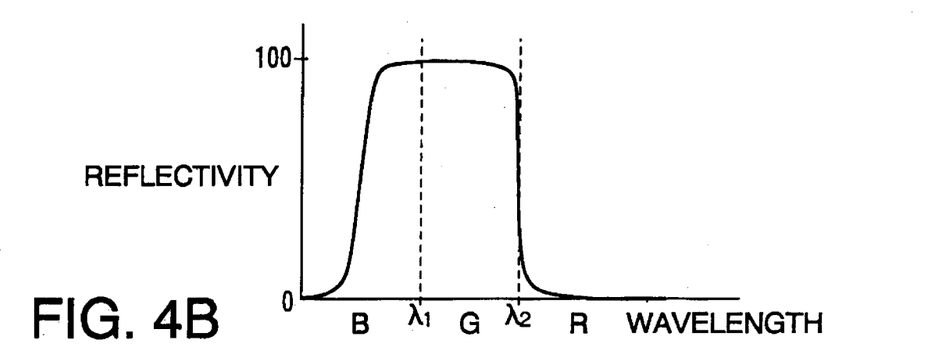
Figure 4C:
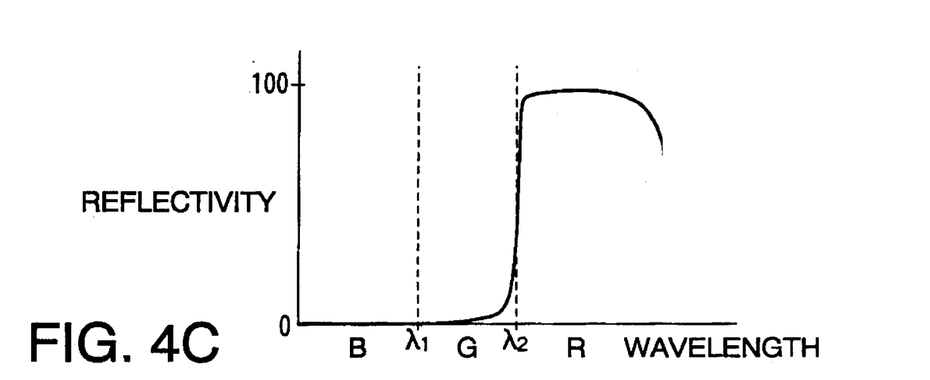

The spectral reflection characteristics of the polarization beam splitters 21, 22, 23 are shown in FIGS. 4A, 4B and 4C, respectively. As shown in FIG. 4A, of the luminous flux generated by the light source unit 10 is incident on the polarization beam splitter 21, the S-polarized light having a wavelength corresponding to blue light is reflected. However, the S-polarized light corresponding to green light and red light, as well as P-polarized light pass through the polarization beam splitter 21, and are incident on the polarization beam splitter 22.

As shown in FIG. 4B, the S-polarized light corresponding to green light is reflected by the polarization beam splitter 22. However, the S-polarized light corresponding to red light, as well as P-polarized light pass through the polarization beam splitter 22, and are incident on the polarization beam splitter 23.

As shown in FIG. 4C, the S-polarized light corresponding to red light is reflected by the polarization beam splitter 23. However, the P-polarized light passes through the polarization beam splitter 23, and is incident on the mirror 24.

Further, the transmission of the P-polarized light through the polarization beam splitters 21, 22, and 23, does not vary with the wavelength of the P-polarized light. Therefore, all of the visible light can be transmitted. Furthermore, if the incident angle of the luminous flux with respect to the polarization surface is set to be close to the Brewster Angle, it will be easier to design and manufacture the polarization separation surface having the maximum polarization separation characteristic.

In the first embodiment, since a cube type prism is used for the polarization beam splatters, the refractive index of the medium, around the polarization separation filter, becomes substantially the same and the Brewster Angle is approximately 45°. Therefore, the LCD projector 60 is designed such that the luminous flux is incident on the polarization separation surface at an incident angle of 45°.

The LCD panels 30 through 32 modulate the respective luminous fluxes with image data provided by a video signal. The LCD panel 30 modulates the S-polarized luminous flux corresponding to blue light which is reflected by the polarization beam splitter 21. Similarly, the LCD panel 31 modulates the S-polarized luminous flux corresponding to green light which is reflected by the polarization beam splitter 22. Further, the LCD panel 32 modulates the S-polarized luminous flux corresponding to red light which is reflected by the polarization beam splitter 23. Furthermore, the brightness LCD panel 33 modulates the P-polarized light which is reflected by the mirror 24.

The LCD panels 30 through 33 are arranged to have equal optical path lengths from the projecting lens 51.

The polarization beam splitter group 40 has a similar constitution as the polarization beam splitter group 20. Thus, the polarization beam splitter 41 reflects the S-polarized luminous flux corresponding to blue light, the polarization beam splitter 42 reflects S-polarized luminous flux corresponding to green light, and the polarization beam splitter 43 reflects the S-polarized luminous flux corresponding to red light.

The P-polarized luminous flux corresponding to the brightness is reflected by the mirror 44 and is transmitted through the polarization beam splitters 41, 42, and 43 to be combined with S-polarized luminous fluxes corresponding to blue, green and red light. The combined luminous flux is projected onto the screen 50 via the projecting lens 51.

Therefore, as described above, in the LCD projector 60 having the above configuration, substantially all of the luminous flux is projected onto the screen. Thus, a bright image is formed on the screen. Further, the brightness of the image is sufficient to allow a visible image to be formed on the screen even in a brightly lit room.

Table 1 shows the conventions of spectrum reflectances of the polarization beam splitters In Table 1 W1, W2, and W3 indicate the wavelength ranges of the S-polarized light reflected by the polarization beam splitters 21, 22, and 23, respectively. In the first embodiment, described above, the combination (1) is used. However, combinations 2 through 4 can also be used.

TABLE 1

| (1) | (2) | (3) | (4) |
|---|---|---|---|
| W1 ≦ λ1 (B) | W1 ≦ λ1 (B) | W1 ≧ λ2 (R) | W1 ≧ λ2 (R) |
| W2 ≦ λ2 (G) | W2 ≧ λ2 (R) | W2 ≦ λ1 (B) | W2 ≦ λ1 (G) |
| W3 (R) | W3 (G) | W3 (G) | W3 (B) |

It is possible to arrange the polarization beam splitter 22, which reflects the S-polarized luminous flux corresponding to green light, to be positioned nearest to the light unit 10. In this case the bandwidth of the spectral reflecting characteristic of the polarization beam splitter 22 must reflect only the luminous flux having a wavelength between the blue-green wavelength $\lambda 1$ and the green-red wavelength $\lambda 2$. However, it is difficult and expensive to achieve this spectral reflecting characteristic using thin film technology.

Therefore, in this embodiment the polarization beam splitter which reflects the luminous flux corresponding to blue light or the polarization beam splitter which reflects the luminous flux corresponding to red light (i.e., a polarization beam splitter which reflects light outside the range of wavelengths between λ1 and λ2), is arranged at a position nearest the light unit 10.

This is because reflection of the luminous flux corresponding to blue light requires only that the spectral reflection characteristic be accurately designed for wavelengths approaching λ1. Similarly, reflection of the luminous flux corresponding to red light requires only that the spectral reflection characteristic be accurately designed for wavelengths approaching λ2.

Further, by providing the polarization beam splitter 21 or 23 for reflecting luminous flux corresponding to either blue light or red light, respectively, at the position nearest the light unit, the polarization beam splitter 22 is required to separate the other two luminous fluxes (i.e., green and red or blue and green, respectively). Therefore, a spectral reflection characteristic of the polarization beam splitter 22 only requires accuracy in filtering light having a wavelength which is close to either the green-red wavelength λ1 or the blue-green wavelength λ2, but not both wavelengths λ1 and λ2.

As described above, in the first embodiment of the LCD projector, the spectral reflection characteristics of each of the polarization beam splitters are designed such that the each polarization beam splitter reflects all the light having a wavelength which is shorter than a predetermined value (i.e., λ1 or λ2). It is therefore easier to manufacture each polarization beam splitter using existing manufacturing technology and coating design.

Figure 5:
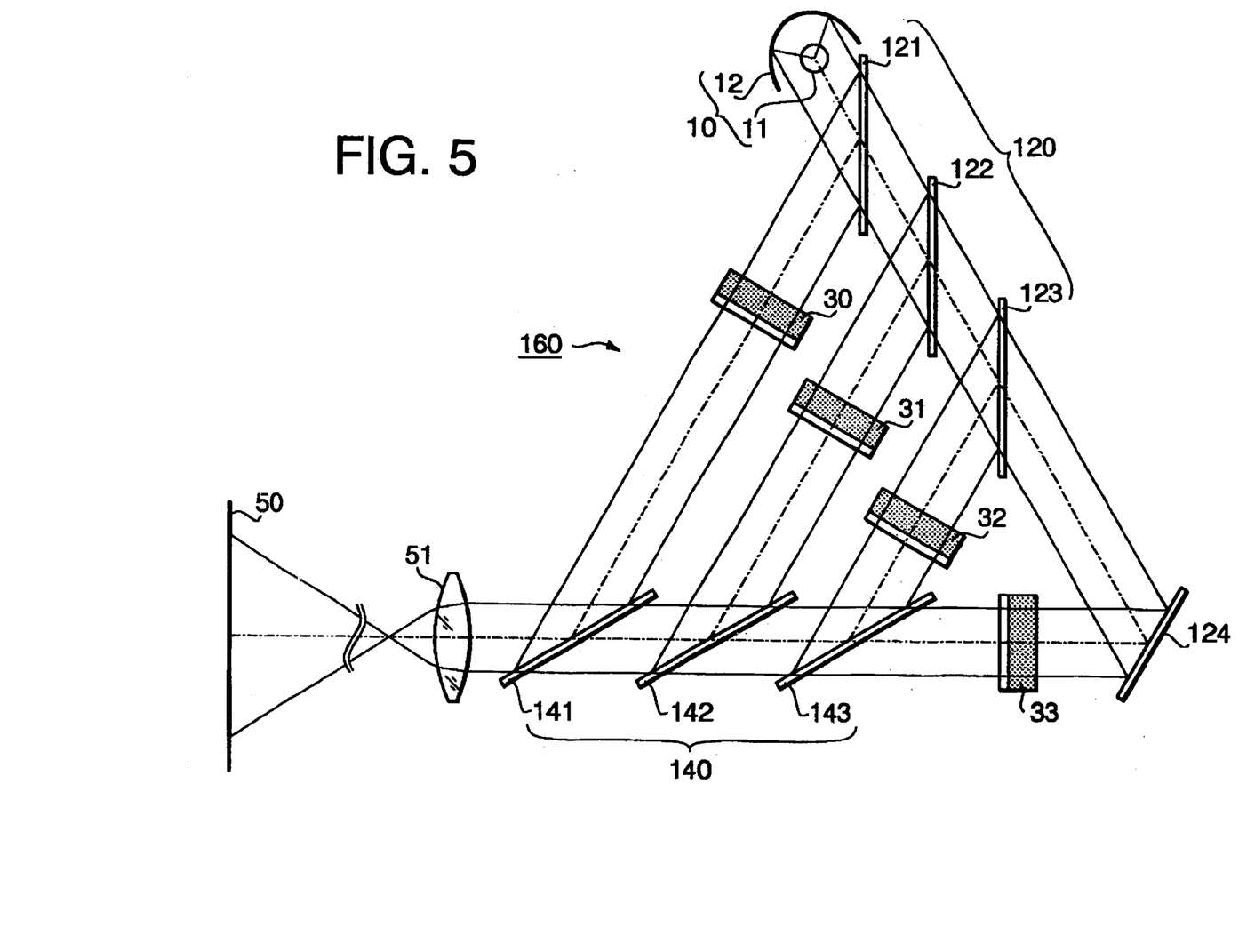
FIG. 5 shows a schematic diagram of a second embodiment of an LCD projector according to the present invention.

FIG. 5 shows a schematic diagram of an optical system of an LCD projector 160 according to a second embodiment of the present invention.

In the second embodiment, a flat type of polarization beam splitter is used instead of the cube prism type of polarization beam splitter used in the first embodiment, described above.

The LCD projector 160 is similar to the LCD projector 60 described above, with the same parts having common reference numerals.

Therefore, the randomly polarized white light generated by the light source unit 10 is color separated by the polarization beam splitter group 120 into three separate S-polarized luminous fluxes (corresponding to the light having wavelengths in the blue, green and red wavelength ranges), and one P-polarized luminous flux (corresponding to the brightness). The three S-polarized luminous fluxes are modulated by the image information, using the LCD panels 30 through 32. The P-polarized luminous flux is reflected by the mirror 124 and then modulated by the LCD panel 33. The modulated luminous fluxes are then recombined into a single luminous flux by the polarization beam splitter group 140, and then projected by the lens 51 onto the screen 50.

The polarization beam splitter groups 120 and 140 will be described in more detail below.

The polarization beam splitter group 120 includes the polarization beam splitters 121, 122, and 123. The polarization beam splitter 121 has spectral reflection characteristics such that the S-polarized luminous flux having a wavelength that is less than the blue-green wavelength λ1 is reflected. Further, all other S-polarized luminous flux and the P-polarized luminous flux are transmitted through the polarization beam splitter 121.

Similarly, the polarization beam splitter 122 has spectral reflection characteristics such that the S-polarized luminous flux having a wavelength that is less than the green-red wavelength λ2 is reflected. Further, all other S-polarized luminous flux and the P-polarized luminous flux are transmitted through the polarization beam splitter 122.

Further, the polarization beam splitter 123 has spectral reflection characteristics such that the remaining S-polarized luminous flux is reflected, while the P-polarized luminous flux is transmitted to the mirror 124.

In case the flat type polarization beam splitter is used, since the medium in front of the polarization surface is air, the ratio of the reflectances of the media on either side of the polarization surface is about 1:1.4 through 1:2.0. Accordingly, the Brewster Angle is in the angular range of 55° to 63°. Therefore in the second embodiment, the incident angle of the luminous flux with respect to each of the polarization beam splitters 121, 122 and 123 is set to 60°.

The luminous fluxes having been transmitted through the LCD panels 30 through 33 are combined by the polarization beam splitter group 140. The polarization beam splitter group 140 includes the polarization beam splitters 141, 142 and 143. In the second embodiment, the spectrum reflection characteristics of the polarization beam splitters 141, 142 and 143, are similar to those of polarization beam splitters 121, 122 and 123, respectively.

As described above, by employing the polarization beam splitters which have the spectrum reflection characteristics which are relatively easily manufactured, the S-polarized light and the P-polarized light can be accurately separated and the disturbance of the image to be projected can be prevented.

Further, by crossing the optical axes at the light source side and at the projecting lens side, the number of mirrors required to reflect P-polarized light can be reduced to one, and therefore in the second embodiment, the number of parts used in manufacturing the LCD projector 160 can be reduced.

Thus, according to the present invention, the luminous flux from the light source can be projected effectively onto the screen and can produce a highly visible image. Further, as the optical system can be constituted by employing the polarization beam splitters which have a stable spectral reflection characteristic, the possibility of the disturbance of the image caused by incomplete polarization separation can be made low, and the cost of the overall optical system can be reduced.

The present disclosure relates to subject matter contained in Japanese Patent Application No. HEI 7-64866 filed on Feb. 28, 1995, which is expressly incorporated herein by reference in its entirety.

What is claimed is:
1. An LCD projector comprising:
   a white light source for emitting a randomly polarized luminous flux;
   a plurality of LCD panels for modulating luminous fluxes that are transmitted therethrough;
   first means for reflecting a first portion of said luminous flux having a first polarization characteristic and a wavelength which is within a first predetermined range of wavelengths, to a first LCD panel of said plurality of LCD panels;
   second means for reflecting a second portion of said luminous flux that is not reflected to said first LCD panel, to a second LCD panel of said plurality of LCD panels, said second portion of said luminous flux having said first polarization characteristic and a wavelength which is within a second predetermined range of wavelengths;

third means for reflecting a third portion of said luminous flux that is not reflected to said second LCD panel, to a third LCD panel of said plurality of LCD panels, said third portion of said luminous flux having said first polarization characteristic and a wavelength which is within a third predetermined range of wavelengths; and fourth means for reflecting a fourth portion of said luminous flux that is not reflected to said third LCD panel, to a fourth LCD panel, said fourth portion of the luminous flux having a second polarization characteristic.

2. The LCD projector according to claim 1, further comprising:

first means for combining said third portion of said luminous flux transmitted through said third LCD panel with said fourth portion of said luminous flux transmitted through said fourth LCD panel, into a first combined luminous flux;

second means for combining said modulated second portion of said luminous flux transmitted through said second LCD panel with said first combined luminous flux, into a second combined luminous flux;

third means for combining said first portion of said luminous flux transmitted through said first LCD panel with said second combined luminous flux, into a third combined luminous flux; and means for projecting said third combined luminous flux onto a screen.

3. The LCD projector according to claim 2, wherein said fourth reflecting means comprises a mirror for reflecting said fourth luminous flux to said fourth LCD panel.

4. The LCD projector according to claim 3, further comprising another mirror for reflecting said fourth portion of said luminous flux transmitted through said fourth LCD panel to said first combining means.

5. The LCD projector according to claim 1, wherein said first portion of said luminous flux reflected by said first reflecting means has a wavelength which is shorter than a first predetermined wavelength, wherein said second portion of said luminous flux reflected by said second reflecting means has a wavelength which is shorter than a second predetermined wavelength, said second predetermined wavelength being longer than said first predetermined wavelength; and wherein said third portion of said luminous flux reflected by said third reflecting means has a wavelength which is longer than said second predetermined wavelength.

6. The LCD projector according to claim 5, wherein said first predetermined wavelength is a blue-green border wavelength, and wherein said second predetermined wavelength is a green-red border wavelength.

7. The LCD projector according to claim 1, wherein said first reflecting means comprises a first polarization beam splitter, said second reflecting means comprises a second polarization beam splitter and said third reflecting means comprises a third polarization beam splitter, each of said first polarization beam splitter, said second polarization beam splitter and said third polarization beam splitter reflecting luminous flux which is polarized such that an electric vector thereof is perpendicular to an incident plane of said first polarization beam splitter, and transmitting luminous flux which is polarized such that an electric vector thereof is parallel to said incident plane.

8. The LCD projector according to claim 7, wherein said first combining means comprises a fourth polarization beam splitter, said fourth polarization beam splitter being identical to said third polarization beam splitter, wherein said second combining means comprises a fifth polarization beam splitter, said fifth polarization beam splitter being identical to said second polarization beam splitter, and wherein said third combining means comprises a sixth polarization beam splitter, said sixth polarization beam splitter being identical to said first polarization beam splitter.

9. The LCD projector according to claim 1, wherein said first reflecting means is arranged such that an angle of incidence of said luminous flux on said first reflecting means is equivalent to the Brewster Angle, and wherein said second reflecting means, said third reflecting means and said fourth reflecting means are arranged to be parallel to said first reflecting means.

10. An LCD projector comprising:

a light source for emitting a luminous flux having randomly polarized white light, a first polarization beam splitter having a spectrum reflection characteristic for reflecting one of red light and blue light of the luminous flux having a first polarization characteristic, and for transmitting a remaining portion of the luminous flux;

a second polarization beam splitter having a spectrum reflection characteristic for reflecting a portion of the luminous flux transmitted by said first polarization beam splitter having green light having said first polarization characteristic, and for transmitting another remaining portion of the luminous flux;

a third polarization beam splitter having a spectrum reflection characteristic for reflecting a portion of the luminous flux transmitted by said second polarization beam splitter having the other of the red light and the blue light having said first polarization characteristic, not reflected by said first polarization beam splitter, and for transmitting a third remaining portion of said luminous flux;

three LCD panels, each of said LCD panels modulating one of the reflected light components; and a fourth LCD panel for modulating a light component having a second polarization characteristic which is transmitted through said third polarization beam splitter.

11. The LCD projector according to claim 10, which further comprises:

a fourth polarization beam splitter for combining light having said first polarization characteristic modulated by a first LCD panel of said three LCD panels, with said light having said second polarization characteristic modulated by said fourth LCD panel to form a first combined luminous flux;

a fifth polarization beam splitter for combining said light having said first polarization characteristic modulated by a second LCD panel of said three LCD panels with said first combined luminous flux, to form a second combined luminous flux;

a sixth polarization beam splitter for combining said light having said first polarization characteristic modulated by a third LCD panel of said three LCD panels with said second combined luminous flux, to form a third combined luminous flux; and means for projecting said third luminous flux onto a screen.

12. The LCD projector according to claim 11, wherein said first polarization beam splitter, said second polarization beam splitter, and said third polarization beam splitter are cube prism elements arranged along the luminous flux emitted from said white light source, and wherein said fourth polarization beam splitter, said fifth polarization beam splitter, and said sixth polarization beam splitter are cube prism elements arranged along the luminous flux incident to said projecting means, and wherein said luminous flux emitted from said white light source is parallel to said luminous flux incident to said projecting means.

13. The LCD projector according to claim 11, wherein said first polarization beam splitter, said second polarization beam splitter, and said third polarization beam splitter are flat type elements arranged along the luminous flux emitted from said white light source, and wherein said fourth polarization beam splitter, said fifth polarization beam splitter, and said sixth polarization beam splitter are flat type elements arranged along the luminous flux incident to said projecting means, and wherein said luminous flux emitted from said white light source intersects said luminous flux incident to said projecting means.

14. The LCD projector according to claim 10, wherein said first polarization beam splitter has a spectrum reflection characteristic such that light having said first polarization characteristic and a wavelength that is less than a first predetermined wavelength is reflected by said first polarization beam splitter.

15. The LCD projector according to claim 14, wherein said second polarization beam splitter has a spectrum reflection characteristic such that light having said first polarization characteristic and a wavelength that is less than a second predetermined wavelength is reflected by said second polarization beam splitter, said second predetermined wavelength being greater than said first predetermined wavelength.

16. The LCD projector according to claim 15, wherein said first predetermined wavelength is a blue-green border wavelength, and wherein said second wavelength is a green-red border wavelength.

17. The LCD projector according to claim 10, wherein said first polarization beam splitter has a spectrum reflection characteristic such that light having said first polarization characteristic and a wavelength that is greater than a first predetermined wavelength is reflected by said first polarization beam splitter.

18. The LCD projector according to claim 17, wherein said second polarization beam splitter has a spectrum reflection characteristic such that light having said first polarization characteristic and a wavelength that is greater than a second predetermined wavelength is reflected by said second polarization beam splitter, said second wavelength being shorter than said first wavelength.

19. The LCD projector according to claim 18, wherein said first predetermined wavelength is a green-red border wavelength, and wherein said second wavelength is a blue-green border wavelength.

20. A method for separating a randomly polarized luminous flux generated by a white light source in an LCD projector into various light components having different wavelength ranges and polarization states, the method comprising:

reflecting a first portion of the luminous flux having a first polarization characteristic and a wavelength which is within a first predetermined range of wavelengths, to a first LCD panel;

reflecting a second portion of the luminous flux that is not reflected to the first LCD panel, to a second LCD panel, the second portion of the luminous flux having the first polarization characteristic and a wavelength which is within a second predetermined range of wavelengths;

reflecting a third portion of the luminous flux that is not reflected to the second LCD panel, to a third LCD panel, the third portion of the luminous flux having the first polarization characteristic and a wavelength which is within a third predetermined range of wavelengths; and reflecting a fourth portion of the luminous flux that is not reflected to the third LCD panel, to a fourth LCD panel, the fourth portion of the luminous flux having a second polarization characteristic.

* * * * *

UNITED STATES PATENT AND TRADEMARK OFFICE
CERTIFICATE OF CORRECTION

PATENT NO. : 5,812,223
DATED : September 22, 1998
INVENTOR(S) : Masato NOGUCHI.

It is certified that error appears in the above-identified patent and that said Letters Patent is hereby corrected as shown below:

At column 9, line 20 (claim 2, line 8) of the printed patent delete "modulated".

Signed and Sealed this

Thirtieth Day of May, 2000

Attest:

Q. TODD DICKINSON

*Attesting Officer*  *Director of Patents and Trademarks*